US006214875B1

(12) United States Patent
Yang

(10) Patent No.: US 6,214,875 B1
(45) Date of Patent: Apr. 10, 2001

(54) ANTICANCER EFFECTS OF SPECIFIC BRANCHED-CHAIN FATTY ACIDS AND RELATED PRODUCTION PROCESS

(76) Inventor: Zhenhua Yang, 3008 Andalucia Dr., West Covina, CA (US) 91791

( * ) Notice: Subject to any disclaimer, the term of this patent is extended or adjusted under 35 U.S.C. 154(b) by 0 days.

(21) Appl. No.: 09/173,681

(22) Filed: Oct. 16, 1998

Related U.S. Application Data

(60) Provisional application No. 60/081,712, filed on Apr. 14, 1998.

(51) Int. Cl.$^7$ .................................................. A61K 31/20
(52) U.S. Cl. .................................. 514/558; 514/2; 514/8; 514/557; 514/560; 426/61; 424/115; 424/116; 424/123
(58) Field of Search .................................. 514/2, 8, 558, 514/560, 557; 426/61; 424/115, 116, 123

(56) References Cited

U.S. PATENT DOCUMENTS

| | | |
|---|---|---|
| 4,877,739 | 10/1989 | Yang . |
| 4,985,466 | 1/1991 | Deguchi . |

FOREIGN PATENT DOCUMENTS

| | | |
|---|---|---|
| 2020633 | 8/1997 | (CA) . |

OTHER PUBLICATIONS

Chemical Abstracts 118:139830, "Higher Fatty Acids as Anticancer Agents and Anticancer Agent Enhancers", Aug. 1995.*
Hansen, et al., "The Branched–chain Fatty Acids of Mutton Fat. The Isolation of (+)–12–methyltetradecanoic Acid and of 13–methyltetradecanoic Acid," *Biochem. J.*, vol. 53, pp. 374–378 (1953).
Kaneda, T., "Fatty Acids of the Genus Bacillus: an Example of Branched–Chain Preference," *Bacteriological Reviews*, vol. 41, No. 2, pp. 391–418, (1977).

Hansen, R.P., Shorland, F.B. and Cooke, N.J. The Branched–Chain Fatty Acids of Mutton Fat, 2. The Isolation of (+)–12–Methyltetradecanoic Acid and of 13–Methyltetradecanoic Acid. Biochem. J. 53:374(1953).
Hansen R.P., Shorland, F.B. and Cooke, N.J. The Branched–Chain Fatty Acids of Butterfat, 4. The Isolation of (+)–12–Methyltetradecanoic Acid and of 13–Methyltetradecanoic Acid. Biochem. J. 57:297 (1954).
Klein, R.A., Halliday, D. and Pittet, P.G. The Use of 13–Methyltetradecanoic Acid as an Indicator of Adipose Tissue Turnover. Lipids 15:572 (1980).
Pittet, P.G. Bessart, T., Jequier, E., Philippossian, G. and Liardon, R. Adipose Tissue Labelling in Man, Using a Structurally–Labelled Fatty Acid as a Tracer. Intern. J.Vit. Nutr. Res. 53:115(1982).
Faung, S.T., Chiu, L. and Wang C.T., Platelet Lysis and Functional Perturbation by 13–Methyl Myristate, the Major Fatty Acid in Flavobacterium Ranacida. Thromb. Res. 81:91 (1996).
Wells, J.M. Butterfield, J.E. and Revear, L.G., Identification of Bacteria Associated with Postharvest Diseases of Fruits and Vegetables by Cellular Fatty Acid Composition: An Expert System for Personal Computers. Phytopathology 83:445 (1993).
Dee, S.B., Karr, D.E. Hollis, D. and Woss, C.W. Cellular Fatty Acids of Capnocytophaga Species. J. Clin. Microbiol. 16:779 (1982).
Heerdt, B.G. Houston,M.A. and Augenlicht, L.H. Potentiation by Specific Short–Chain Fatty Acids of Differentiation and Apoptosis in Human Carcinoma Cell Lines. Cancer Res. 54:3288 (1994).

* cited by examiner

*Primary Examiner*—Frederick Krass
(74) *Attorney, Agent, or Firm*—Oblon, Spivak, McClelland, Maier & Neustadt, P.C.

(57) ABSTRACT

A group of specific branched-chain fatty acids, with significant anticancer effects on human and animals; methods of making using either chemical synthesis or biosynthesis methods; and methods of treating cancer.

23 Claims, 7 Drawing Sheets

(3 of 7 Drawing Sheet(s) Filed in Color)

ANTICANCER EFFECTS OF SPECIFIC BRANCHED-CHAIN FATTY ACIDS AND RELATED PRODUCTION PROCESS

This application claims the benefit of U.S. Provisional Application No. 60/081,712, filed Apr. 14, 1998, which is incorporated by reference herein.

BACKGROUND OF THE INVENTION

1. Field of the Invention

The present invention relates to a group of compounds, i.e., specific branched-chain fatty acids, with significant anticancer activities, and methods of treating cancer. The invention also relates to a process of producing fermentation products containing said specific branched-chain fatty acids, using specific bacteria strains, preferably in industrial facilities.

2. Description of the Background

Carcinoma is one of the most serious diseases threatening human's health and life. So far the predominant treatments to cancer patients are radiotherapy and chemotherapy. Both have certain toxicity or side effects on humans while suppressing cancer cell growth or killing cancer cells. Therefore extensive investigations have been carried out in order to find an effective anti-carcinogen with minimum side effects and toxicity.

In 1987, when the inventor cultured K562 leukemia cell lines in the laboratory, cells in a culture flask were found to have completely disappeared 48 hours after being contaminated by a kind of rod bacteria. Those rod bacteria were then intentionally harvested and purified, and incubated in soybean media with appropriate inorganic salts. It was found in later animal studies that the fermentation solution effectively inhibited tumor growth with no toxicity or side effects. In the decade since then, thousands of cancer patients, including advanced stage cancer patients, have been treated with the oral liquid developed from this fermentation solution. These include leukemia, tongue cancer, colorectal cancer, breast cancer, prostate cancer, lung cancer, gastric cancer, hepatocarcinoma, melanocarcinoma, renal cancer, esophagus cancer and pancreas cancer patients. Most of them have responded to the oral liquid, such as by symptom improvement, tumor shrinkage or even complete disappearance. Many of these patients are still alive today. The cases included patients in China, Japan, Korea, the United States, and many other countries.

In order to discover the active components in the fermentation solution that play a key role in killing cancer cells, persistent investigations have been carried out for the last ten years. In this period many books and papers were published worldwide trying to explain the anticancer activity of this fermentation solution. Most of these reports suggested that some soybean isoflavones (e.g. genistein, daidzein and saponin) from the soybean media contributed to the anticancer activities of this fermentation solution. On the other hand, some clinical trials indicated that the anticancer activities of soybean isoflavones were not great enough to explain the anticancer effects of the fermentation solution. The inventor has isolated many compounds from the fermentation solution and revealed that the anticancer activities of the solution were largely contributed by 13-methyltetradecanoic acid and 12-methyltetradecanoic acid. Further investigations discovered that other members of the family of branched-chain fatty acids also had significant tumor-inhibition effects. So far there are no other reports in the literature regarding the anticancer activity of specific branched-chain fatty acids.

SUMMARY OF THE INVENTION

The present invention relates to a group of compounds, i.e., specific branched-chain fatty acids, with significant anticancer activities, and methods of treating cancer using these compounds. Comprehensive biochemical and morphological tests have demonstrated that these activities are associated with induction of programmed cancer cell death (apoptosis). Very importantly, the specific branched-chain fatty acids do not kill normal cells. In animal studies, intraperitoneal injection of 13-methyltetradecanoic acid daily up to 800 mg/kg to mice did not reach the $LD_{50}$ level (50% lethal dose).

The specific branched-chain fatty acids can be, but are not limited to, those obtained by synthesis, or by isolation from said fermentation products. Particularly, the present invention relates to the fermentation products containing these specific branched-chain fatty acids, which have the capability of inhibiting the growth of cancer cells without any toxic or side effects. The present invention also relates to a process of producing fermentation products containing the specific branched-chain fatty acids, using specific bacteria strains, preferably in industrial facilities.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE INVENTION

Figure 1A:
FIGS. 1A and 1B show the morphological changes of SNU-423 human hepatocellular carcinoma cells undergoing apoptosis under a light microscope; A: untreated; B: treated with 13-methyltetradecanoic acid (60 µg/ml) for 24 hours.

Definitions of the Specific Branched-chain Fatty Acids

The present invention relates to a group of compounds, i.e., specific branched-chain saturated and unsaturated fatty acids, with significant anticancer activities. The branched-chain saturated fatty acids can be described by the formula:

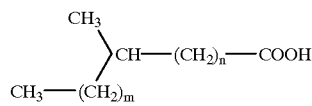

where n and m are independently integers, and n+m is between 0 and 46, inclusive. Preferably, m is 0 or 1, and n is 7–16.

The branched-chain unsaturated fatty acids of the present invention have the above formula, except that m or n is at least 2, and at least one $CH_2$—$CH_2$ group in $(CH_2)_m$ or $(CH_2)_n$ is replaced with a CH=CH group.

The term "iso-Cx", as used in the present invention, means a branched-chain saturated fatty acid having x carbons and n=x–4, m=0 in the above formula. The term "anteiso-Cx" means the compound having x carbons and n=x–5, m=1 in the above formula. For example, 13-methyltetradecanoic acid is expressed as "iso-C15" and has the formula

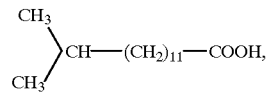

12-methyltetradecanoic acid is expressed as "anteiso-C15" and has the formula:

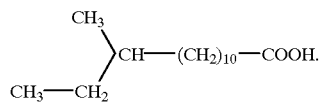

An example of an unsaturated branched-chain fatty acid of the present invention is 15-methylhexadecenoic acid:

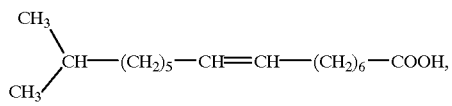

otherwise known as iso-17:1 ω9c.

The present invention also includes pharmaceutically acceptable salts of said saturated and unsaturated branched-chain fatty acids, which are obtained by reaction with inorganic bases, such as sodium hydroxide, and have the ability to inhibit cancer cell growth.

The present invention also includes pharmaceutically acceptable lipoproteins of said saturated and unsaturated branched-chain fatty acids, which are obtained by conjugation with proteins, including polypeptides and oligopeptides, and have the ability to inhibit cancer cell growth. Such lipoproteins are well known in the art.

The specific branched-chain fatty acids of the present invention can be obtained by, but not limited to, isolation from fermentation or incubation products using specific bacteria, or by electrochemical synthesis, or by extraction from natural materials.

Having generally described this invention, a further understanding can be obtained by reference to certain specific examples which are provided herein for purposes of illustration only and are not intended to be limiting unless otherwise specified.

I. Demonstration of Anticancer Activity of Specific Branched-chain Fatty Acids

EXAMPLE 1

Anticancer Activity In Vitro
Samples
iso-C15, including extracted and synthesized The extracted iso-C15 was isolated by HPLC (High Performance Liquid Chromatography) from the fermented solution (fermented using the specific bacteria, *Stenotrophomonas maltophilia* Q-can, and media and production process in present invention).

The synthesized iso-C15 was purchased from Sigma Chemical Company (St. Louis, Mo.)

The other specific branched-chain fatty acids tested include:

10-methylundecanoic acid (iso-C12),
11-methyllauric acid (iso-C13),
12-methyltridecanoic acid (iso-C14),
11-methyltridecanoic acid (anteiso-C14),
12-methyltetradecanoic acid (anteiso-C15),
14-methylpentadecanoic acid (iso-C16),
13-methylpentadecanoic acid (anteiso-C16),
15-methylpalmitic acid (iso-C17),
16-methylheptadecanoic acid (iso-C18),
15-methylheptadecanoic acid (anteiso-C18),
17-methylstearic acid (iso-C19),
18-methylnonadecanoic acid (iso-C20).

All the samples above were purchased from Sigma Chemical Company.
Cell lines
Human Leukemia Cell Line K562 and Human Gastric Cancer Cell Line SGC7901
Methods MTT assay was performed to test the cytotoxicity. The K562 and SGC7901 cells were maintained in exponential growth in RPMI 1640 medium supplemented with 15% heat-inactivated newborn calf serum. The cells were plated at a density of $2\times10^4$ cells/100 μl medium/well into 96-well plate with medium containing samples in five final concentrations (7.5, 15, 30, 60 and 90 μg/ml) for iso-C15 (either synthesized or extracted) and one final concentration (30 μg/ml) for the others. The media in control wells contained no samples. The cells were incubated at 37° C. in a highly humidified incubator under 5% $CO_2$ atmosphere for 24 hours. The supernatant was removed by fast inversion of the plate. 20 μl of 5 mg/ml MTT solution were added into each well. Incubation was continued for 4 hours. DMSO 100 μl/well was added and the plate was vibrated for 10 minutes. $A_{570nm}$ was read at the Immunoreader BioTek EL311S.

The inhibition rate (%)=1−(mean $A_{570nm}$ in test wells/mean $A_{570nm}$ in control wells)

Results

TABLE 1

Inhibitory rate (%) of synthesized iso-C15 * on cell growth

| Cell line | 90 μg/ml | 60 μg/ml | 30 μg/ml | 15 μg/ml | 7.5 μg/ml |
|---|---|---|---|---|---|
| K562 | 85.3 | 83.1 | 71;6 | 50.1 | 26.2 |
| SGC7901 | 68.4 | 63.1 | 50.5 | 27.5 | — |

* the sample was dissolved with 10% ethanol.

TABLE 2

Inhibitory rate (%) of extracted iso-C15 * on cell growth

| Cell line | 90 μg/ml | 60 μg/ml | 30 μg/ml | 15 μg/ml | 7.5 μg/ml |
|---|---|---|---|---|---|
| K562 | 87.2 | 83.7 | 72.2 | 51.2 | 27.1 |
| SGC7901 | 68.8 | 62.1 | 51.2 | 28.1 | — |

* the sample was dissolved with 10% ethanol.

TABLE 3

Inhibitory rate (%) of specific branched-chain fatty acids* on K562 cell growth

| Sample | iso-C12 | iso-C13 | iso-C14 | iso-C16 | iso-C17 | iso-C18 |
|---|---|---|---|---|---|---|
| % | 70.69 | 71.03 | 72.15 | 71.58 | 70.79 | 68.39 |
| Sample | iso-C19 | iso-C20 | anteiso-C15 | anteiso-C14 | anteiso-C16 | anteiso-C18 |
| % | 69.15 | 62.58 | 73.10 | 72.59 | 70.68 | 71.73 |

*the concentration of branched-chain fatty acids was 30 μg/ml; the sample was dissolved with NaOH solution to adjust to pH 7.5.

EXAMPLE 2

Determination of $ID_{50}$, $ID_{75}$ and $ID_{90}$

Samples

The extracted iso-C15 was isolated by HPLC from the fermented solution (fermented using the specific bacteria, Stenotrophomonas maltophilia Q-can, and process of the present invention, infra). The samples were prepared by dissolving them in NaOH solution (adjusted to pH7.5) and 0.5% Tween 80 (Sigma Chemical Company, St. Louis, Mo.).

Cell Lines

All tumor cell lines were purchased from American Type Culture Collection (ATCC, Manassas, VG) and were cultured as recommended by vendor. Human PBLs were separated from whole blood of healthy individuals by using Ficoll-Hypaque gradients. They were maintained in suspension in RPMI 1640 with 10% plasma from the same individuals. All cell cultures were incubated in a $CO_2$ atmosphere (5%) at 37° C.

Seven human tumor cell lines were studied. K-562 human leukemia and SNU-1 human gastric carcinoma cell lines were cultured in suspension in RPMI 1640 supplemented with 10% heat-inactivated fetal bovine serum (FBS). MCF-7 human breast adenocarcinoma, DU-145 human prostate carcinoma, SNU-423 human hepatocellular carcinoma, HCT 116 human colon carcinoma, and Hl688 human small cell lung carcinoma cell lines were propagated as adherent cells in RPMI 1640 supplemented with 10% heat-inactivated FB S (for SNU-423 and Hl688), or in McCoy's 5a medium with 10% heat-inactivated FBS (for HCT 116), or in minimum Eagle's medium with 10% heat-inactivated FBS (for MCF-7 and DU-145).

Methods

All cells in adherent culture were initiated at $5×10^4$ cells/well in 96-well microplates and treated immediately with iso-C15 at different concentrations (0, 1.5, 3.0, 6.0, 15.0, 30.0, and 60.0 μg/ml) diluted with medium. Both untreated and solvent (NaOH and Tween 80) treated cells served as controls. The treated cells were incubated for 48 hours at 37° C. After incubation, the supernatants were removed and the cells were trypsinized and collected prior to viability assessment by trypan blue dye exclusion.

PBLs, K-562 and SNU-1 cells in suspension culture were seeded in 96-well microplates at a density of $5×10^4$ cells/well for K-562 and SNU-1, and $1×10^5$ cells/well for PBLs. iso-C15 were diluted with medium to provide different concentrations (0, 1.5, 3.0, 6.0, 15.0, 30.0, and 60.0 μg/ml). Both untreated and solvent (NaOH and Tween 80) treated cells served as controls. After incubation for 48 hours at 37° C., cells were collected directly from the wells for viability assessment.

The $ID_{50}$, $ID_{75}$ and $ID_{90}$ were determined in duplicate in every set of experiments, and each experiment was repeated three times under identical conditions. $ID_{50}$, $ID_{75}$ and $ID_{90}$ were defined as the concentration of iso-C15 required to kill 50, 75 or 90%, respectively, of cells (compared with that in untreated cells) and computed using CalcuSyn for Windows software (Biosoft, Cambridge UK) based on Median Effect method by Dr. T. C. Chou.

Results

The cytotoxic activity of iso-C15 was quantified by determining $ID_{50}$, $ID_{75}$ and $ID_{90}$ (μg/ml or μM) in several human hematological and solid tumor cell lines. It is indicated from Table 4 that iso-C15 was active in all tumor cell lines studied. The strongest cytotoxic activities were for MCF-7 human breast adenocarcinoma and K-562 human leukemia. The activities were less for Hl688 human small cell lung carcinoma and HCT 116 human colon carcinoma cell lines. In contrast, iso-C15 is not toxic against normal human peripheral blood lymphocytes at concentrations lethal to tumor cells.

TABLE 4

Cytotoxicity of iso-C15 on human tumor and normal cells in vitro

| cell line | cell type | $ID_{50}$(μg/ml) | $ID_{75}$(μg/ml) | $ID_{90}$(μg/ml) |
|---|---|---|---|---|
| MCF-7 | breast carcinoma | 10.03 ± 0.97 | 15.99 ± 1.28 | 25.49 ± 1.68 |
| K-562 | leukemia | 11.45 ± 1.82 | 22.27 ± 4.60 | 43.57 ± 6.71 |
| DU145 | prostate carcinoma | 13.98 ± 2.15 | 40.43 ± 5.72 | 81.87 ± 8.85 |
| H1688 | lung carcinoma | 15.08 ± 1.92 | 35.03 ± 3.59 | 61.37 ± 8.06 |
| HCT-116 | colon carcinoma | 18.49 ± 6.23 | 67.96 ± 8.25 | 108.65 ± 13.35 |

TABLE 4-continued

Cytotoxicity of iso-C15 on human tumor and normal cells in vitro

| cell line | cell type | $ID_{50}$(μg/ml) | $ID_{75}$(μg/ml) | $ID_{90}$(μg/ml) |
|---|---|---|---|---|
| SNU-1 | gastric carcinoma | 20.77 ± 2.47 | 47.43 ± 4.95 | 80.49 ± 10.03 |
| SNU-423 | hepato-carcinoma | 24.26 ± 3.98 | 70.46 ± 9.36 | 120.77 ± 15.82 |
| PBL | normal human lymphocytes | >400 | | |

EXAMPLE 3
Induction of Apoptosis of Cancer Cells In Vitro

Samples iso-C15 was isolated by HPLC from the fermented solution (fermented by the specific bacteria, *Stenotrophomonas maltophili* Q-can and the process of the present invention, infra). 12-methyltetradecanoic acid (anteiso-C15) was purchased from Sigma Chemical Co. (St. Louis, Mo.). The samples were prepared by dissolving them in NaOH solution (adjusted to pH7.5) and 0.5% Tween 80 (Sigma Chemical Company, St. Louis, Mo.).

Cell Lines

Same as Example 2, above.

Methods

The apoptosis (programmed cell death) of cancer cells induced by specific branched-chain fatty acids was confirmed by: (a) morphology, visualizing morphological changes indicative of apoptosis; (b) flow cytometry, identifying the cells undergoing apoptosis and discriminating apoptosis from necrosis; (c) in situ cell death detection kit, POD, detecting apoptosis induced DNA strand breaks at single cell level.

A flow cytometer (FACScan) with Consort 30 software for gating analysis (Becton Dickinson, San Jose, Calif.) was used. The Apoptosis Detection kit (R&D Systems) was used to quantitatively determine the percentage of cells undergoing apoptosis by virtue of their ability to bind annexin V and exclude propidium iodide (PI). Cells were washed in cold phosphate-buffered saline (PBS) twice and resuspended in binding buffer. Fluorescent labeled annexin V and PI were added to the cells. The cells undergoing apoptosis, expressing phosphotidyiserine on the outer leaflet of cell membranes, would bind annexin V. The cells in later stage of apoptosis or necrosis, with a compromised cell membrane, would allow PI to bind to the cellular DNA. The resulting cells were immediately analyzed by flow cytometer equipped with a single laser emitting excitation light at 488 nm. The annexin V and PI generated signals can be detected in signal detector FL1 and FL2, respectively. Three potential populations of cells can be presented in FL1/FL2 pattern: live cells would not stain with either fluorochrome (zone 3), necrotic and later apoptotic cells would stain with both fluorochromes (zone 2) while cells undergoing apoptosis would stain only with annexin V (zone 4).

In Situ Cell Death Detection Kit, POD (Mannheim Boehringer GmbH) was used to detect the individual apoptotic cells. Cleavage of genomic DNA during apoptosis may yield double-stranded, low molecular weight DNA fragments as well as single strand breaks in high molecular weight DNA. Those DNA strand breaks can be identified by labeling free 3'-OH termini with modified nucleotides in an enzymatic reaction. In this kit terminal deoxynucleotidyl transferase (TdT) is used to label free 3'-OH ends in genomic DNA with fluorescein-dUTP. The incorporated fluorescein is visualized under fluorescence microscope directly. The incorporated fluorescein can also bind to antifluorescein antibody POD and be detected by substrate reaction. Stained cells can be analyzed under a light microscope.

Results

Morphological Changes

The apoptosis of cancer cells is morphologically characterized by cell shrinkage, chromatin condensation, nuclear fragmentation, and extensive formation of membrane blebs and apoptotic bodies.

Figure 1B:
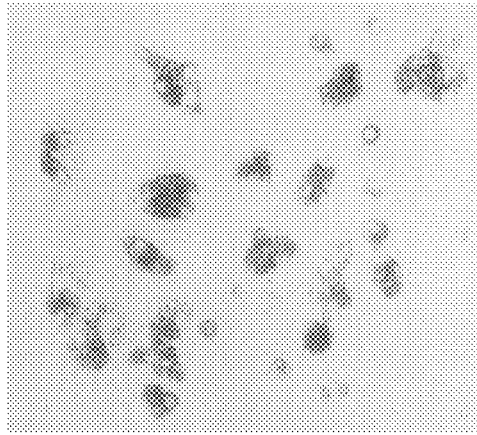
Figure 2A:
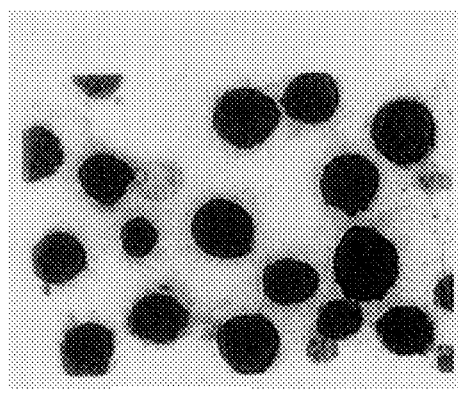
FIGS. 2A and 2B show the morphological changes of SNU-1 human gastric carcinoma cell lines stained with H&E under a light microscope; A: untreated; B: treated with 13-methyltetradecanoic acid (60 µg/ml) for 8 hours.
Figure 2B:
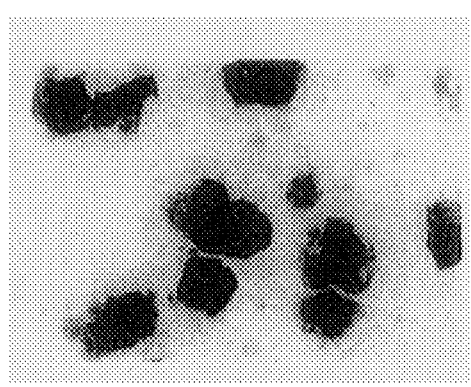
Figure 3A:
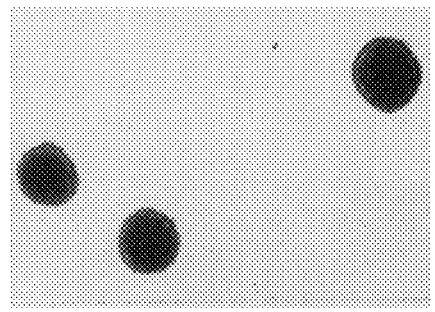
FIGS. 3A and 3B show the morphological changes of DU-145 human prostate carcinoma cell lines stained with H&E under a light microscope; A: untreated; B: treated with 13-methyltetradecanoic acid (60 µg/ml) for 8 hours.
Figure 3B:
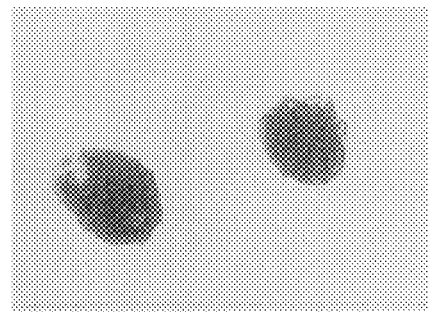

FIG. 1 illustrates the morphological changes of cancer cells undergoing apoptosis in a light microscope. Cultured SNU-423 human hepatocellular carcinoma cells treated with anteiso-C15 in 60 μg/ml for 24 hours (FIG. 1B) exhibited cell volume decrease due to shrinkage and bubbles inside the cell, compared to an untreated control (FIG. 1A). Cultured SNU-1 human gastric carcinoma cell lines were treated with anteiso-C15 in 60 μg/ml for 8 hours, and cellular morphology was evaluated in preparations stained with H&E (FIG. 2B). Compared to an untreated control (FIG. 2A), chromatin condensation and cytoplasmic granularity were noted. Cultured DU-145 human prostate carcinoma cell lines were treated with iso-C15 in 60 μg/ml for 8 hours, and cellular morphology was evaluated in preparations stained with H&E dye (FIG. 3B). Compared to an untreated control (FIG. 3A), membrane blebs were noted.

Flow Cytometry

Figure 4A:
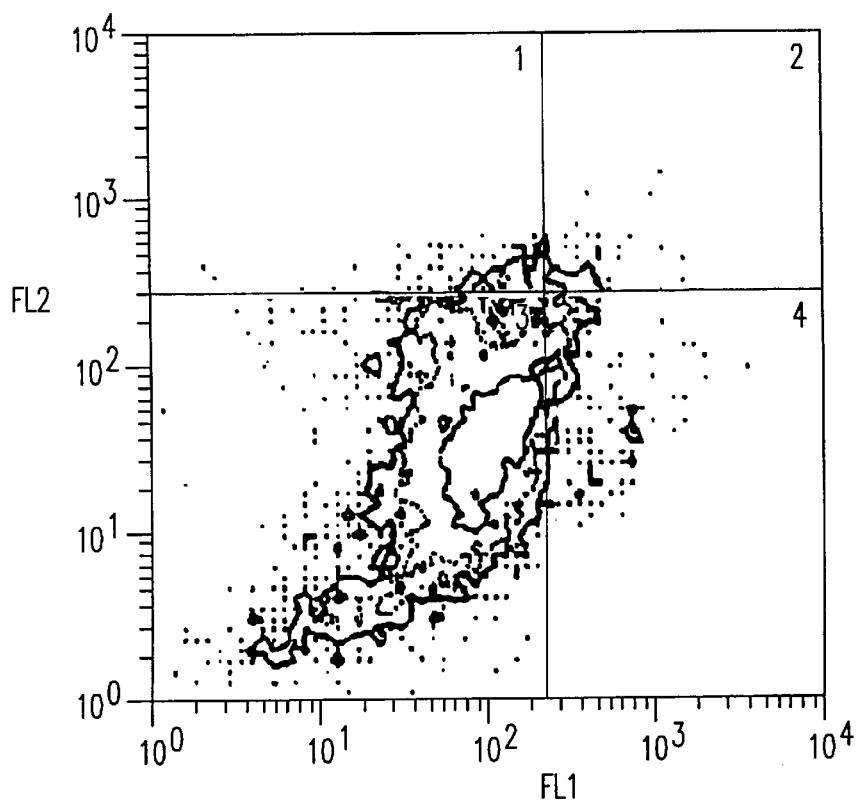
FIGS. 4A and 4B show flow cytometric analysis of K562 human leukemia cells; A: untreated; B: treated with 13-methyltetradecanoic acid (30 µg/ml) for 24 hours.
Figure 4B:
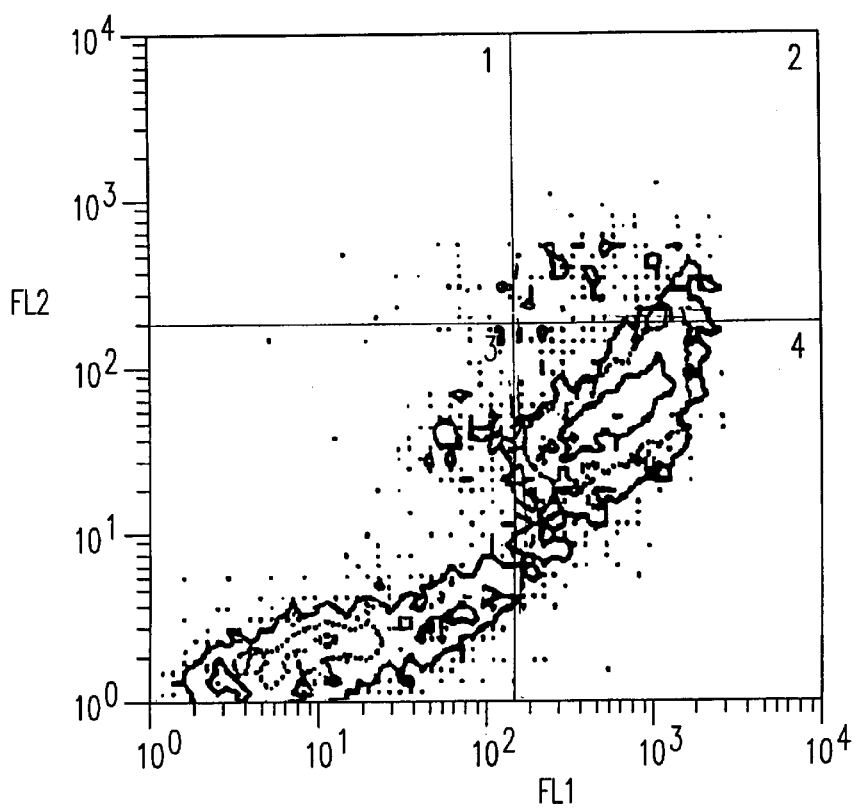
Figure 5A:
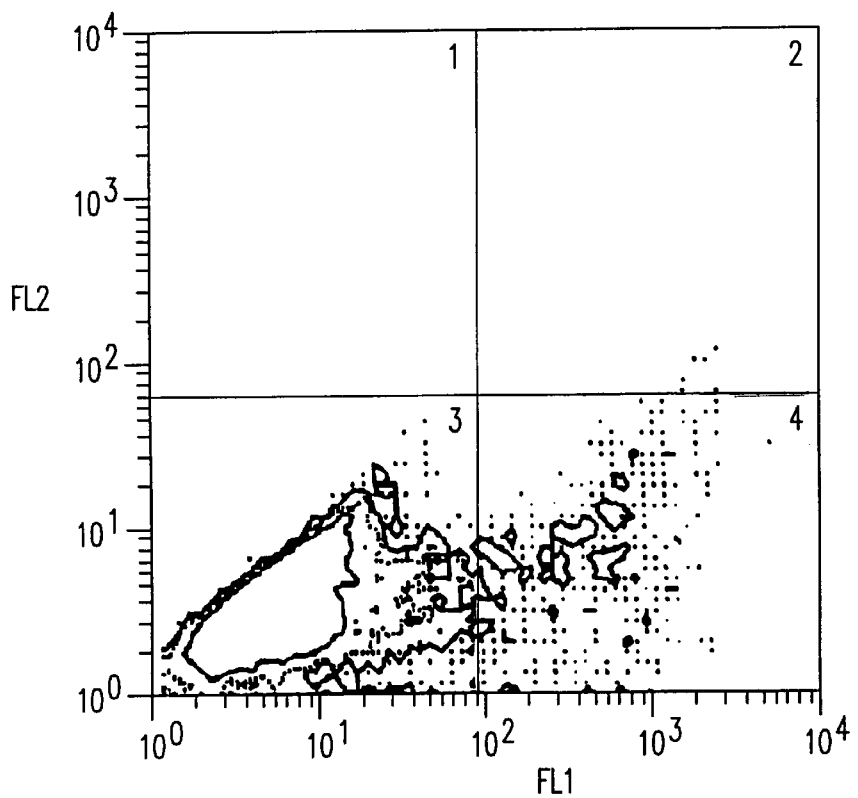
FIGS. 5A, 5B and 5C show flow cytometric analysis of MCF-7 human breast adenocarcinoma cells; A: untreated; B: treated with 12-methyltetradecanoic acid (60 µg/ml) for 4 hours; C: treated with 12-methyltetradecanoic acid (60 µg/ml) for 24 hours.
Figure 5B:
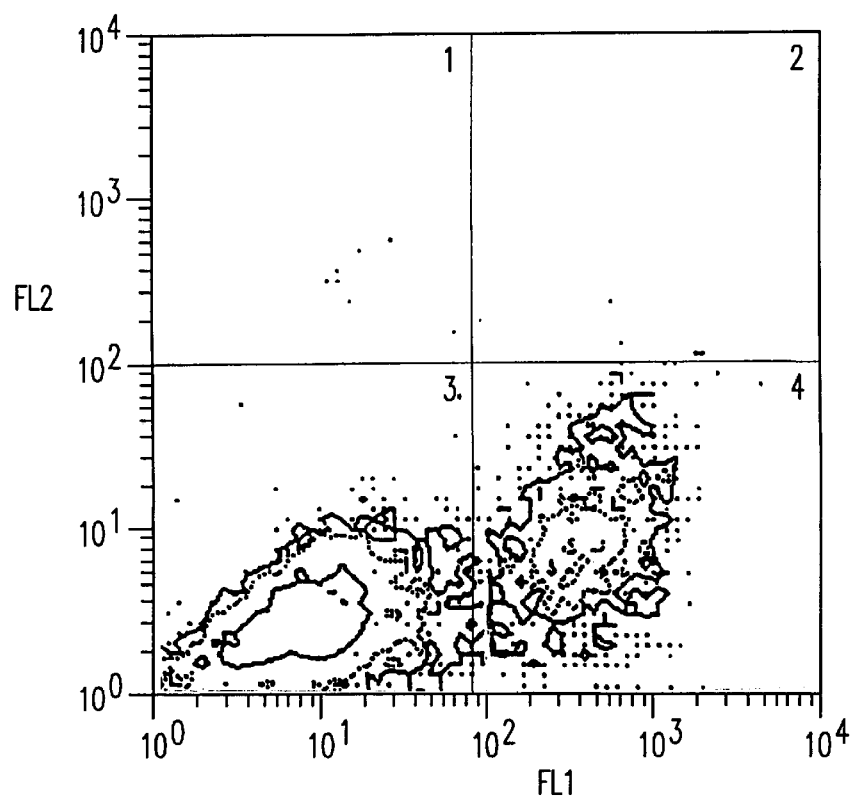
Figure 5C:
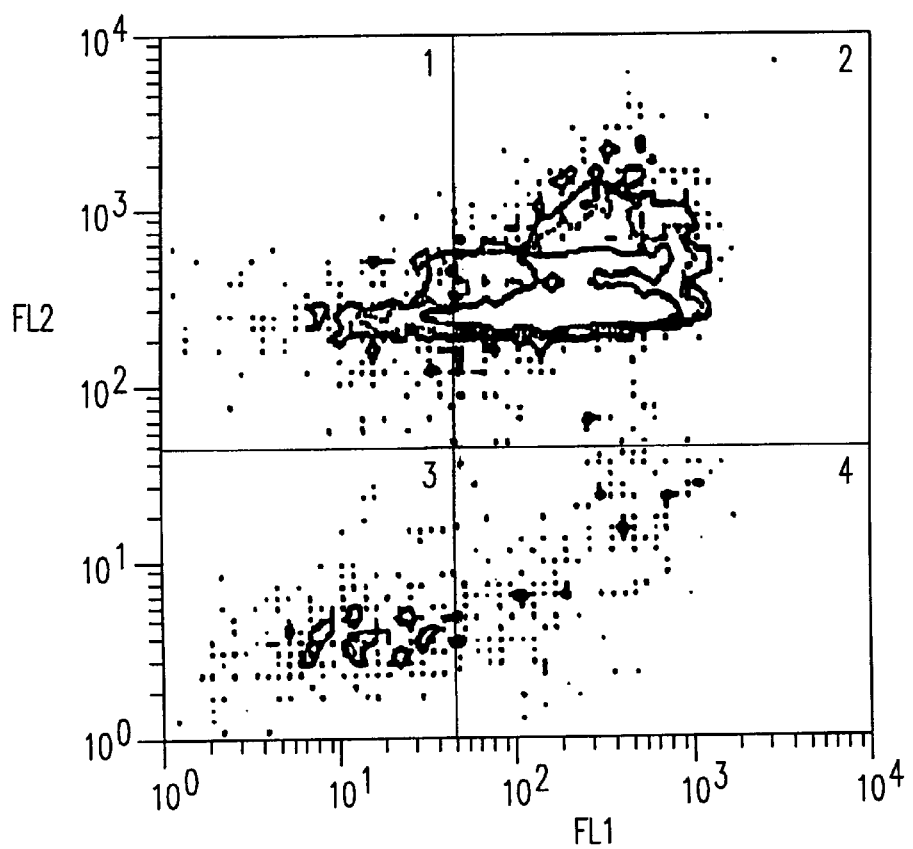
Figure 6A:
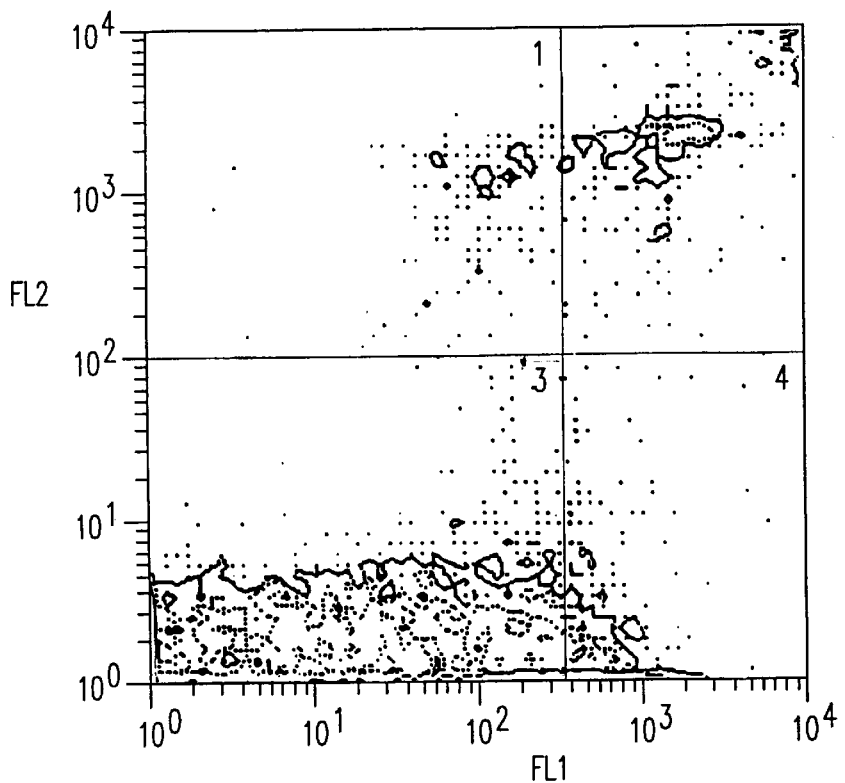
FIGS. 6A and 6B show flow cytometric analysis of normal human peripheral blood lymphocytes (PBLs); A: untreated; B: treated with 13-methyltetradecanoic acid (60 µg/ml) for 24 hours.
Figure 6B:
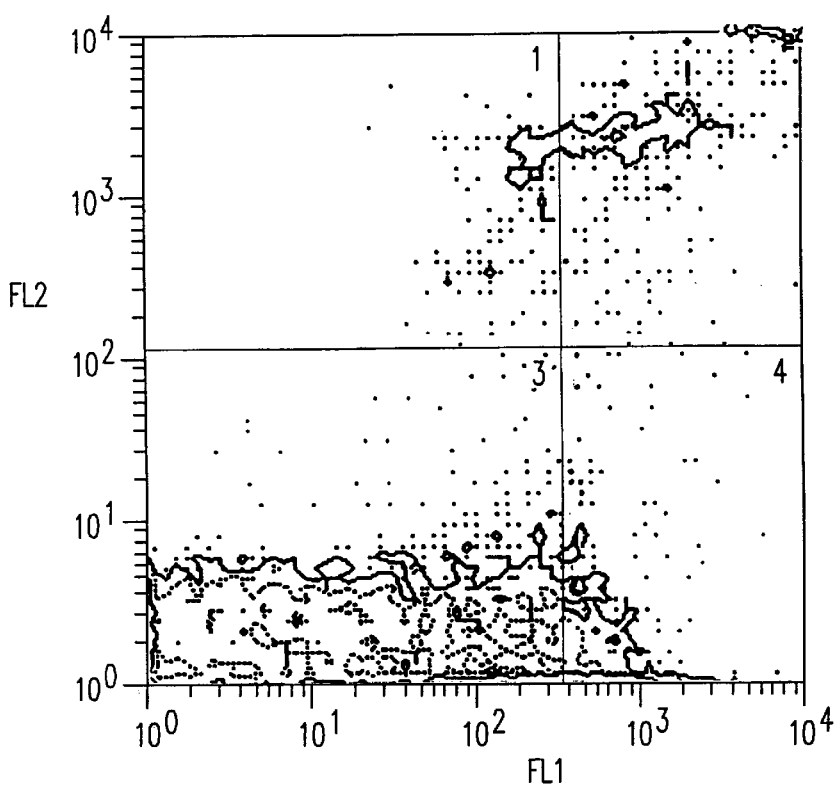

At least $10^4$ cell events were analyzed. The FL1/FL2 pattern of untreated K562 human leukemia cells (FIG. 4A) revealed the expected distribution of cells in zone 3. After treatment of K562 cells with iso-C15 (30 μg/ml) for 24 hours (FIG. 4B), the majority of the cells were undergoing apoptosis (zone 4, Annexin V positive and PI negative). The kinetic behavior of anteiso-C15 in MCF-7 human breast adenocarcinoma cells was evidenced by FIGS. 5A, 5B and 5C, for treatment of MCF-7 cells with anteiso-C15 (60 μg/ml) for 0, 4 and 24 hours, respectively. After treatment of anteiso-C15 for 4 hours, many cells were undergoing apoptosis (zone 4, FIG. 5B), while after 24 hours the majority of cells had already died (later stage of apoptosis, zone 2, FIG. 5C). The flow cytometric analysis of untreated normal human PBLs (FIG. 6A) and treated PBLs with iso-C15 (60 μg/ml) for 24 hours (FIG. 6B) resulted in nearly identical FL1/FL2 patterns (zone 3, viable and not undergoing apoptosis), revealing no significant effects by iso-C15 on normal human lymphocytes.

In Situ Cell Death Detection

Four human tumor cell lines, K-562 human leukemia, SNU-1 human gastric carcinoma cell lines, MCF-7 human breast adenocarcinoma and Hl688 human small cell lung carcinoma cell lines, as well as Human PBLs were treated with iso-C15 (60 μg/ml).

Figure 7A:
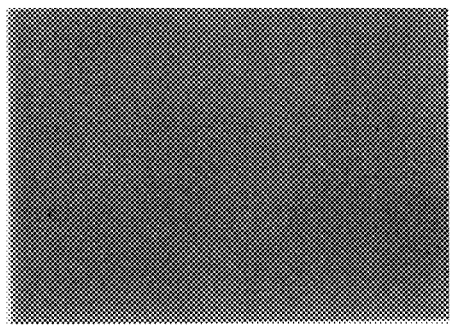
FIGS. 7A and 7B show detection of apoptotic SNU-1 cell lines added with TUNEL-(TdT-mediated dUTP nick end labeling) reaction mixture under a fluorescence microscope; A: untreated; B: treated with 13-methyltetradecanoic acid (60 µg/ml) for 8 hours.
Figure 7B:
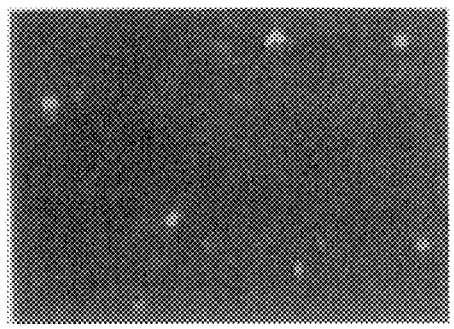

SNU-1 cells treated with iso-C15 for 8 hours were added with TUNEL-reaction mixture and incubated 60 min at 37° C. After washing with PBS for three times, cell morphology was analyzed directly under fluorescence microscopy. Several yellow fluorescent spots of apoptotic cells were noted in cells treated for 8 hours (FIG. 7B), comparing to untreated ones (FIG. 7A).

Figure 8A:
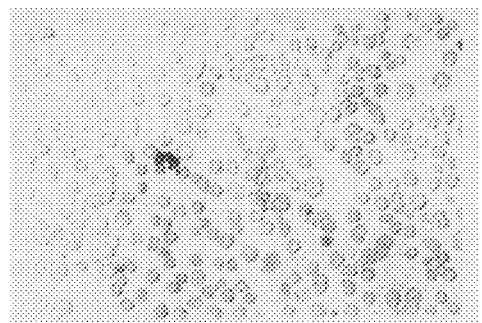
FIGS. 8A, 8B and 8C, show detection of apoptotic K-562 cell lines added with peroxidase (POD) and substrate under a light microscope; A: untreated; B: treated with 13-methyltetradecanoic acid (60 µg/ml) for 2 hours; C: treated with 13-methyltetradecanoic acid (60 µg/ml) for 4 hours.
Figure 8B:
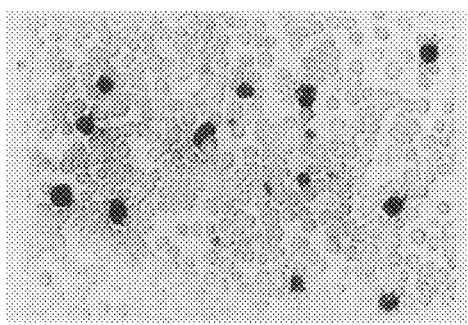
Figure 8C:
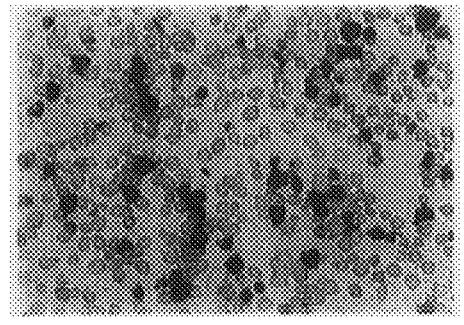
Figure 9A:
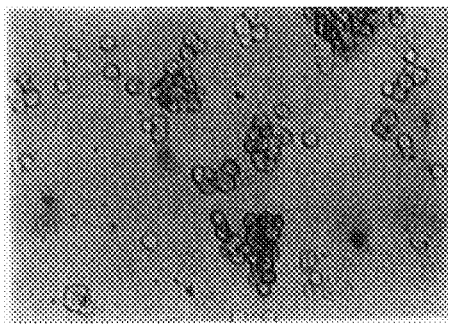
FIGS. 9A and 9B show detection of apoptotic H1688 cell lines added with POD and substrate under a light microscope; A: untreated; B: treated with 13-methyltetradecanoic acid (60 μg/ml) for 8 hours.
Figure 9B:
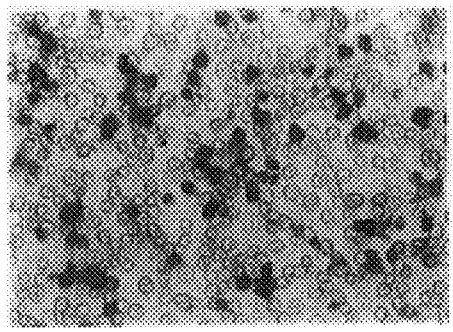
Figure 10A:
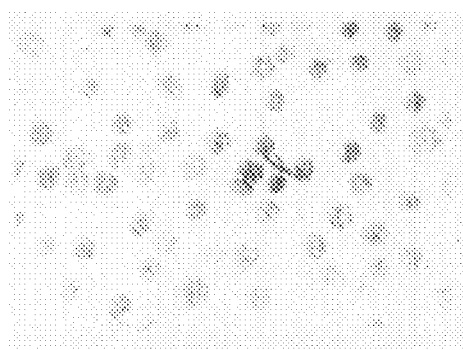
FIGS. 10A and 10B show detection of apoptotic DUI45 cell lines added with POD and substrate under a light microscope; A: untreated; B: treated with 13-methyltetradecanoic acid (60 μg/ml) for 8 hours.
Figure 10B:
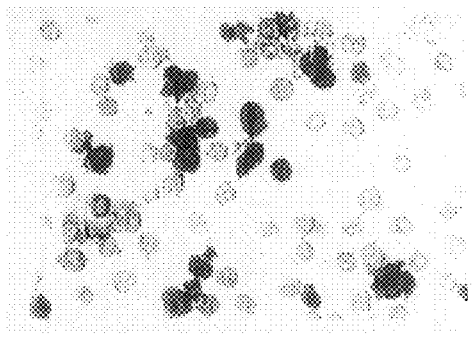
Figure 11A:
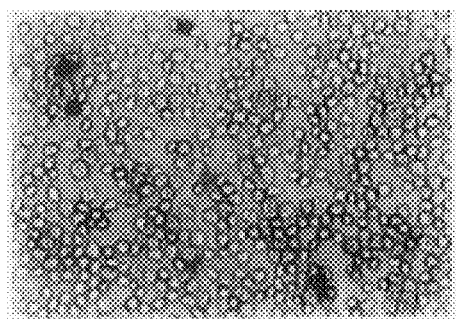
FIGS. 11A and 11B show normal human PBLs added with POD and substrate under light microscope; A: untreated; B: treated with 13-methyltetradecanoic acid (60 μg/ml) for 8 hours.
Figure 11B:
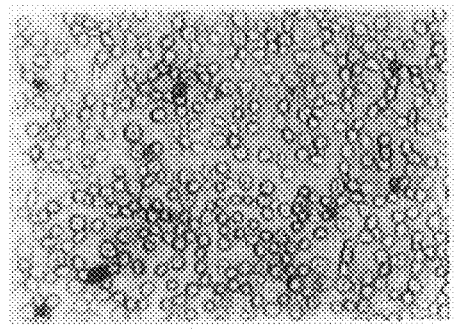

Hl688, K-562 and DU145 human cancer cells and normal human PBLs were added with POD and incubated 30 min at 37° C., washed three times with PBS, then reacted with substrate AEC and incubated for 10 min at room temperature. The cells were analyzed under a light microscope. Comparing K-562 leukemia cells untreated (FIG. 8A) and treated for 2 and 4 hours (FIGS. 8B and 8C), it was found that some cells started apoptosis (stained red) 2 hours after treatment and the number of apoptotic cells increased with exposure time. The apoptotic Hl688 cancer cells (stained red) were found after 8 hours of treatment (FIG. 9B) comparing to untreated (FIG. 9A). Some stained apoptotic DU145 cancer cells were shown 8 hours after treatment (FIG. 10B) and no stained cells in an untreated control (FIG. 10A). In contrast, untreated and 8-hour treated PBLs were almost the same (FIGS. 11A and 11B), and few stained apoptotic cells were seen. It is evidenced that iso-C15 induces apoptosis of cancer cells but not normal human cells.

weights and tumor weights were measured. The tumor inhibition rates (TIR) were determined by comparing the mean tumor weight of the test groups (T) with that of the control group (C) and expressed as a (C-T)/C percentage, and were analyzed by Student's test for statistical significance.

Results

The results (Table 5) showed the significant anti-tumor activity of iso-C15 against human breast carcinoma MCF7 with a tumor inhibition rate of 71.6% at i.p. injection every other day over a 26-day period.

TABLE 5

Effects of iso-C15 on Human Breast Carcinoma Xenograft MCF7 Implanted into Subcutaneous Area of Nude Mice

| group | dose | route | mice No. in./fi. | body weight im./fi. | tumor weight mean ± SD(g) | TIR(%) | P |
| --- | --- | --- | --- | --- | --- | --- | --- |
| NS | — | i.p. | 6/6 | 20.1/17.7 | 1.09 ± 0.28 | — | |
| iso-C15 | 60 mg/kg | i.p. | 6/6 | 20.4/19.6 | 0.19 ± 0.13 | 82.2 | <0.05 |

EXAMPLE 4
Anticancer Activity In Vivo
A. Determination of $LD_{50}$
Materials and Methods 13-methyltetradecanoic acid (iso-C15) purchased from Sigma (St. Louis, Mo.) was prepared by dissolving in NaOH solution and then in 0.35% Tween 80 with pH7.5.

ICR mice weighing 20.5–22.5 g of both sexes were treated with iso-C15 i.p. qd×3 in test groups and with solvent of same dose as in a control group. The doses ranged from 10 to 800 mg/kg of iso-C15 and two mice were included in each dose group (10 mg/kg, 20 mg/kg, 40 mg/kg, 80 mg/kg, 160 mg/kg, and 800 mg/kg). The general condition of these mice were monitored daily for seven days.

Results

No mice died after seven-day administration of iso-C15 of dose up to 800 mg/kg. It is shown that iso-C15 is basically not toxic to mice and 50% lethal dose ($LD_{50}$) was not determined.

B. Therapeutic Effects of iso-C15 on Human Breast Carcinoma MCF7 Xenografted into Nude Mice
Material and Methods 13-methyltetradecanoic acid (iso-C15) purchased from Sigma (St. Louis, Mo.) was prepared by dissolving in NaOH solution and then in 0.35% Tween 80 with pH7.5.

Female Balb/c-nu/nu athymia mice, 6 weeks old, weighing 18–22 g, housed in specific pathogen free (SPF) condition throughout the course of the experiment.

Subcutaneous transplantation of human breast carcinoma MCF7 was carried out under aseptic condition. Several tumor-growing wells were cut into fragments (approximately 0.18×0.18×0.20 mm in size), and injected s.c. into the right mammary fat pad of each animal with trocar. Seven days after inoculation (designated day 0), the mice bearing the tumor about 14 mm³ in size were selected and randomized into control and test groups of six mice each. On day 1 and day 2, the mice in the test group were injected i.p. with prepared iso-C15 at 60 mg/kg daily. The same treatment was given every other day after day 4. The mice in the control group were administered the same dose of normal saline (NS) under the same schedule. The last administration was on day 26 (total 14 administrations). Surgery was performed under ether anesthesia, and animals were sacrificed by spinal elongation on day 28. The body II. Production Process of Specific Branched-chain Fatty Acids The present invention includes methods of making said specific branched-chain fatty acids with anticancer activities.

The specific branched-chain fatty acids of the present invention can be isolated from natural resources occurring including, but not limited to, the organisms containing the specific branched-chain fatty acids, such as animal fats or phytol of green plants.

The specific branched-chain fatty acids of the present invention can also be synthesized by chemical or biological methods. The classical Kolbe's synthesis methods of branched-chain fatty acids are well known and a specific example of a method for electrosynthesis of 13-methyltetradecanoic acid is provided in the example below. The biosynthesis methods for making the specific branched-chain fatty acids of the present invention are fermentation or incubation processes using specific bacteria strains containing a high percentage of specific branched-chain fatty acids in their cellular lipids. A process for making a fermentation solution containing specific branched-chain fatty acids and having anticancer functions is also provided in the examples below.

EXAMPLE 5
Electrolytical Synthesis of 13-Methyltetradecanoic Acid 13-methyltetradecanoic acid is synthesized electrolytically from isovaleric acid and methyl hydrogen dodecanedioate in methanolic solution, based on Kolbe electrolysis.

Dimethyl dodecanedioate was prepared from dodecanedioic acid by esterification with 5 parts v/w methanol containing 5% w/v concentrated sulfuric acid. The dimethyl ester, after purification by vacuum fractional distillation, was converted to the mono-ester using the theoretical quantity of kalium hydroxide in anhydrous methanol. The methyl hydrogen dodecan-1,12-dioate was purified by distillation.

The electrolytic coupling reaction was carried out with mono-ester and a 2-fold molar excess of isovaleric acid dissolved in methanol containing sodium methoxide, using 2×10 cm² platinum electrodes. The reaction mixture was stirred and maintained at 50° C. by water cooling until the solution became alkaline. Electrode polarity was reversed every 30 min to prevent the built-up of deposits on the electrode surfaces.

After electrolysis the reaction mixture was cooled to room temperature and the by-products, dimethyl docosanedioate, which precipitated was removed by filtration. The filtrate was acidified with acetic acid and the methanol removed by rotary evaporation under reduced pressure. The crude methyl 13-methyltetradecanoate was purified by fractional distillation. Finally the methyl ester was hydrolyzed by refluxing with excess 10% w/v sodium hydroxide in ethanol/water (50:50, v/v). After cooling and acidification, the free acid was extracted with diethyl ether and purified by vacuum distillation.

EXAMPLE 6
Process for Making a Fermentation Solution Containing Specific Branched-chain Fatty Acids A process for making a fermentation solution containing a high percentage of specific branched-chain fatty acids is exemplified below.

The starter cultures grow in a slant agar medium for 24 hours first, then are inoculated onto the liquid medium in the culture flask and cultured on the incubator shaker for 24 hours. Next, the liquid cultures in the flask are inoculated onto a seeding tank at an inoculating rate of 0.1–0.5% (w/w). The cultures, after fermenting in the seeding tank for 24 hours, are replaced onto production fermenters to ferment for 48 hours, with aseptic airflow passing the mass. Generally, the magnification ration from seeding tank to production fermenter is about ten. The incubation conditions are aeration rate of 1:0.6–1.2 (mass/air) v/v in, agitation speed of 180–260 rpm, and the temperature of 28–38° C.

After the incubation is finished, the resulting culture solution is autoclaved at 100° C. for 30 minutes, and then the harvested solution can be packaged and autoclaved at 120° C. The resulting product is an oral nutritional liquid with anticancer and salutary functions for human use.

Alternative products can be obtained by a different procedure including, but not limited to, the method below. After the incubation is finished, an appropriate amount of hydrochloric acid can be added to the resulting culture solution to lower the pH to 3–4, and it is autoclaved at 100° C. for 30 minutes and the cooled solution is finally centrifuged. The resulting supernatant, in which soy saponin is the predominant component, can be used to manufacture a nutrient drink with various tastes. Then the same volume of 95% aqueous ethyl alcohol and the same volume of 2 N NaOH can be added to the resulting precipitate, which is then agitated and then heated at 100° C. After cooling and centrifuging, while collecting the resulting supernatant for later use; the same volume of 1 N HCl can be added to the remainder precipitate and heated for 5 minutes at 80° C. After cooling and centrifuging, the resulting supernatant is collected. The two fractions of supernatants are combined together and the pH adjusted to 9.0, to thereby obtain a concentrated oral nutritional liquid product containing various branched-chain fatty acids, and soy isoflavones such as saponin, daidzein, genistein, and other anticancer substances.

Another procedure is, after the incubation is completed, directly atomize and dry the solution into a powder product, and encapsulate the powder into capsules or make tablets.

The specific branched-chain fatty acids can be isolated from the fermented solution using well-known methods in the art for isolating cellular fatty acid. The isolated active branched-chain fatty acids are reprocessed in various formulations. The formulations of the present invention comprise at least one specific branched-chain fatty acid or its pharmaceutically acceptable salt including sodium salt. They can be contained in an ampule for injection or transfusion, especially for advance stage cancer patients. They may also be mixed with a carrier, or diluted by a carrier, or enclosed or encapsulated by a digestible carrier in the form of a capsule, sachet, cachet, paper or other container or by a disposable container such as an ampule. The carrier or diluent may be a solid, semi-solid or liquid material, which serves as a vehicle, excipient or medium for the active therapeutic substance.

In the process described above, soybean media are used. The components are listed by weight with water making up the reminder. Proper amounts of trace elements necessary for the human body in addition to said nutritional components are added.

| Soybean medium | |
|---|---|
| Soybean | 5–10% |
| or soybean milk or bean cake (by soybean wt.) | 5–15% |
| Yeast extract | 0.02–0.5% |
| or yeast powder | 0.02–0.5% |
| $CaCO_3$ | 0.05–0.25% |
| $K_2HPO_4$ | 0.02–0.10% |
| $MgSO_4$ | 0.01–0.05% |
| NaCl | 0.01–0.04% |
| $Na_2MoO_4$ | 5.0–30 ppm |
| $ZnSO_4$ | 2.5–15 ppm |
| $CoCl_2$ | 5.0–20 ppm |

In addition to the bacteria which have been identified as containing a high percentage of branched-chain fatty acids, such as the genus Stenotrophonionas, Xanthomonas, Flavobacterium, Capnocytophaga, Alteromonas, Cytophage, Bacillus, Chryseobacterium, Empdobacter, Aurebacterium, Sphinggobacterium, Staphylococcus and Pseudomonas, the bacteria of the present invention also include all other bacteria strains containing branched-chain fatty acids.

The products in the form of oral liquids, capsules, tablets or injections, produced using said bacteria and media, with the process of making of the present invention, have anticancer functions and other nutritional effects for human and animals.

III. Anticancer Function of Fermentation Solutions Containing Specific Branched-chain Fatty Acids The said fermentation solutions are produced using specific bacteria strains, which contain a high percentage of branched-chain fatty acids, and nutritive media, such as soybean media, and processes of the present invention. The fermentation solution contains various specific branched-chain fatty acids with significant anticancer activity, and other nutritional composites from soybean or other media and bacteria metabolite. To demonstrate their anticancer function, the following animal experiments and clinical trials are presented. As an example of said fermentation solutions, in the following experiments, the fermentation solution, named Q-can oral liquid, was used.

Q-can oral liquid was produced using *Stenotrophomonas maltophilia* strain Q-can as the production strain, while using the soybean medium above and the process of making of the present invention. Parallel animal experiments and clinical trials were also conducted using its atomized capsule product. The same conclusions were obtained as for Q-can oral liquid product.

The production strain, *Stenotrophomonas maltophilia* Q-can, has all the identifying characteristics of the sample on deposit with American Type Culture Collection, 10801 University Boulevard, Manassas, Va. 20110-2209, and assigned ATCC 202105. The bacterial characteristics was identified by ATCC as following:

The cellular morphology is motile, non-sporing, Gram negative, and aerobic rods.

The colony morphology is the following: Colonies at 24 hours on ATCC medium #3 (nutrient agar) were I. ~90% circular (approximately 1 mm in diameter) with entire margins and convex elevation, rough surface, semi-translucent, light beige color; II, ~10% small circular (<1 mm in diameter), entire margins, convex elevation, semi-translucent, smooth surface and darker than I. Same characteristics were found when grown on ATCC medium #18 (T-soy agar), #44 (BHI agar) and #260 (Sheep blood agar). Both colonies were characterized and found to be the same.

The cellular fatty acid composition of *Stenotrophomonas maltophilia* Q-can is the following:

| Fatty Acid (% of total) | | | |
|---|---|---|---|
| straight-chain acid* | | branched-chain acid** | |
| 10:0 | 0.48 | i11:0 | 3.21 |
| 14:0 | 3.14 | i13:0 | 0.50 |
| 15:0 | 0.33 | i15:0 | 39.34 |
| 16:0 | 5.52 | a15:0 | 7.44 |
| 16:1 ω9c | 3.37 | i15:1 | 1.02 |
| 16:1 ω7c | 12.58 | i16:0 | 0.88 |
| hydroxy acid | | i17:0 | 3.68 |
| 3OH-10:0 | 0.12 | i17:1 ω9c | 5.27 |
| 3OH-i11:0 | 1.51 | i19:0 | 0.33 |
| 3OH-i12:0 | 2.68 | | |
| 3OH-i13:0 | 3.57 | | |
| 2OH-13:0 | 0.29 | | |

*The number to the left of the colon refers to the number of carbon atoms, the number to right refers to the number of double bonds.
**i = iso fatty acids, a = anteiso fatty acids.

Since the fatty acid composition of bacteria is influenced by biosynthesis conditions including temperature and pH, the data above may be considered as a typical value.

The typical fatty acid contents in 500 ml of Q-can oral liquid are the following:

| straight-chain acid | | branched-chain acid | |
|---|---|---|---|
| 10:0 | 2.0–2.7 mg | i11:0 | 11.2–15.4 mg |
| 12:0 | 2.9–4.0 mg | i15:0 | 106.0–145.8 mg |
| 14:0 | 13.0–17.7 mg | i16:0 | 3.1–4.3 mg |
| 15:0 | 2.8–3.8 mg | i17:0 | 12.4–17.0 mg |
| 16:0 | 251.7–346.1 mg | i19:0 | 2.2–3.0 mg |
| 17:0 | 2.9–4.0 mg | a15:0 | 23.4–32.1 mg |
| 18:0 | 75.6–104.0 mg | i17:1 ω9c | 4.1–5.7 mg |
| 20:0 | 5.5–7.6 mg | | |
| 12:1 ω8c | 4.3–5.9 mg | hydroxy acid | |
| 16:1 ω7c | 21.0–28.9 mg | 3OH-i11:0 | 6.3–8.6 mg |
| 18:1 ω9c | 488.8–672.0 mg | 3OH-12:0 | 12.0–16.5 mg |
| 18:2 ω6c | 825.9–1135.6 mg | 3OH-i13:0 | 13.2–18.1 mg |

A. Animal Studies

EXAMPLE 7
Acute Toxicity Test of Q-can Oral Liquid
Materials and Methods

Q-can oral liquid; ICR mice weighing 20.5–22.5 g.

Based on the preliminary test which could not determine 50% lethal dose (LD50), twenty ICR mice (half each sex), weighing 20.5–22.5 g in fasting, were given intragastrically with the most endurable capacity of 3 ml Q-can oral liquid per mouse for four times within 24 hours (6a.m., 10a.m., 4p.m., and 10p.m.)
Results It was observed that all the tested mice were less active five minutes after every administration, and returned to normal about one hour later. Three mice suffered from diarrhea one or two days after the administration, but none of tested mice died within the following seven days. After the course of treatment, the tested mice were sacrificed and dissected. Visual observation showed no abnormality in internal organs. This limited test indicated that Q-can oral liquid had no toxic effects, even when large doses were taken acutely. Based on the conversion of body surface area, this dose corresponds to 4642 ml Q-can oral liquid per day for an adult weighing 70 kg.

EXAMPLE 8
Subacute Toxicity Test of Q-can Oral Liquid
Materials and Methods

Q-can oral liquid; Kunming mice weighing 22–24 g.

Twenty-four mice (half each sex) were randomly divided into a control group and a test group, and were administrated intragastrically with the normal saline in the control group and Q-can oral liquid in the test group at a dosage of 0.8 ml per day for 21 days. On the 22nd day, two mice randomly selected from each group were scarified; the paraffin sections of their viscera were made for microscopic examination.
Results No pathologic changes in internal organs were found by either visual observation or observation under microscope. The remaining ten mice in each group were further observed for seven additional days. No mice died in this observation period. This test showed that intragastrical administration of Q-can oral liquid for 21 consecutive days did not result in toxicity or pathologic changes in mice.

EXAMPLE 9
Long-term Toxicity Test of Q-can Oral Liquid
Material and Methods

Q-can oral liquid; Forty male and forty female Spraque-Dawley rats weighing 60±0.75 g were supplied by Sino-English Joint Ventured Shanghai Sipure-Bikai Experimental Animal Co. Ltd.

Eighty mice were randomly divided into four groups: a high-dose group (20 ml/kg Q-can oral liquid); a mid-dose group (10 ml/kg Q-can oral liquid); a low-dose group (5 ml/kg Q-can oral liquid) and a control group (10 ml/kg normal saline). The samples were given intragastrically once a day for three months. Over the course of the experiment, behavior, appetite, gastrointestinal reaction and body weight of the rats were recorded. The index of blood routine, blood platelet, electrocardiogram, liver function and renal function were measured. The tested rats were sacrificed and dissected after three-month administration. Visual and pathological examinations were made for their main organs including heart, liver, spleen, lung, kidney, stomach, jejunum and brain.
Results Generally speaking, the tested rats were well, no abnormal behavior, no gastrointestinal reaction, good appetite. The curve of weight increase of the test group was similar to the control group (p>0.05). The electrocardiograph examination result was normal. The hematology (including blood routine and blood platelet) was not statistically different between the test group and control group (p>0.05). The liver function (including ALT and TTT) and the renal function (including BUN and Cr) showed no obvious changes either (p>0.05). Although the creatinine of the test group was a bit higher, it was still in the normal range. The pathological section examination of the main organs showed that the cell structure and histomorphology in the test group were not obviously different from those in the control group. It is concluded that Q-can oral liquid can be used safely, based on the fact that continuous administration had no toxicity reactions.

EXAMPLE 10
Enhancement of the Effectiveness of Chemotherapeutic Drugs Materials and Methods Q-can oral liquid; mouse liver cancer HAC cell line; male Kunming mice weighing 20–25 g; commercial cyclophosphamide (CP)

Forty mice were randomly divided into 5 groups. In three test groups, 36%, 60% and 100% Q-can oral liquids (diluted with water) were given, respectively, while water was given in both control groups. On the 8th day, 0.2 ml HAC cancer cell suspensions ($10^7$/ml) were injected into the abdominal cavities of each mouse under aseptic condition. On the 1st, 3rd and 5th days after injection, CP (50 mg/kg) was injected i.p. into the mice in all test groups and positive control group. From the 9th day after injection, normal feeding was resumed as before the test. Date of death of each mouse was recorded, and the average life span and the rate increase in life span were calculated. The rate of increase in life span (ILS %) is as following:

$$\frac{\text{Life span of test group} - \text{life span of control group}}{\text{Life span of control group}} \times 100\%$$

Results

The results below (Table 6) showed the enhancement of anticancer effect of chemotherapeutic drug, CP, by combining treatment with Q-can oral liquid. The average life span mice in the control group (without drug) was only 10.63±1.03 days, while that in the positive control group (only taking CP) was 13.06±3.03 days, with ILS of 22.86%. The combination of Q-can oral liquid (with dosage of 60% and 100%) and CP increased the effectiveness of CP, as evidenced by increased average ILS and increased numbers of mice that survived over 17 days (60% prolonged). Therefore the ILS rate by CP treatment has been increased 56.78% and 143.86% by combination with 60% and 100% Q-can oral liquid, respectively. The difference was statistically significant.

TABLE 6

Q-can oral liquid enhanced the effectiveness of CP for liver cancer

| group | drug | life span | mice No (>17d) | prolonged days | ILS % | p* |
|---|---|---|---|---|---|---|
| 1 | — | 10.63 ± 1.03 | 0 | — | — | |
| 2 | 36% Q-can + CP | 12.38 ± 2.37 | 1 | 1.75 ± 2.05 | 16.46 | <0.10 |
| 3 | 60% Q-can + CP | 14.44 ± 3.54 | 2 | 3.94 ± 2.87 | 35.84 | <0.02 |
| 4 | 100% Q-can + CP | 16.56 ± 3.96 | 6 | 5.94 ± 2.96 | 55.75 | <0.01 |
| 5 | CP | 13.06 ± 3.03 | 1 | 2.44 ± 2.58 | 22.86 | <0.05 |

*compared with Group 1 (control group)

EXAMPLE 11
Tumor Inhibition Effects on Mouse Lewis Lung Tumor
Materials and Methods Concentrated Q-can oral liquid (containing specific branched-chain fatty acids 3.6 mg/ml); Female F1 mice (C57/B1 and DBA/2) weighing 18–22 g; Lewis mouse lung tumor.

The mice of the test group were administrated with concentrated Q-can oral liquid at a daily dose of 36 mg specific branched-chain fatty acids per kg weight for 10 days before transplantation of Lewis mouse lung tumor. All the mice were transplanted subcutaneously in the subaxillary region with a piece of Lewis tumor of approximately 2 mm in diameter. The treatments of intraperitoneal injection of chemotherapy drug Cytoxan (CTX) in 30 mg/kg were given once a day after transplantation over an 8 day period for the positive control group. The treatments for the normal control group were daily injection of normal saline for 8 days. The administration of concentrated Q-can oral liquid for the test group was initiated 10 days before tumor transplantation and continued for another 8 days. Finally all the animals were sacrificed by spinal elongation. Tumors were excised and body and tumor weights were recorded.

Results

The significant inhibition effect of Q-can oral liquid was shown in the test data (Table 7) Although the inhibition rate of the positive control group (chemotherapy drug CTX i.p. injection) was higher than the test group, it is noticed that viability of the positive control (70%, only 8-day period)

was lower than the test group (100%, 18–28 days), implying toxicity of CTX. As oral administration is expected to be less effective than intraperitoneal injection, change in route of administration or increase in dosage should enhance the tumor inhibitory rate of Q-can oral liquid.

TABLE 7

Effects of Q-can Oral Liquid on Mouse Lewis Lung Carcinoma Xenograft Implanted into Subcutaneous Area of Nude Mice

| group | dose | route | mice No. in./fi. | body weight in./fi. | tumor weight mean ± SD(g) | TIR(%) | p |
|---|---|---|---|---|---|---|---|
| NS | — | i.p. | 12/11 | 21.2/22.5 | 1.90 ± 0.96 | — | |
| CTX | 30 mg/kg | i.p. | 10/7 | 21.2/20.3 | 0.71 ± 0.36 | 62.6 | <0.01 |
| Q-can | 36 mg/kg | i.p. | 10/10 | 20.9/21.9 | 1.11 ± 0.46 | 41.6 | <0.05 |

EXAMPLE 12

Tumor Inhibition Effects on Human Gastric Adenocarcinoma SGC-7901 Xenografted into Nude Mice Material and Methods Female Balb/c-nu/nu athymia mice, 6 weeks old, weighing 18–22 g, housed in specific pathogen free (SPF) condition throughout the course of experiment; concentrated Q-can oral liquid contains 3.6 mg/ml specific branched-chain fatty acids; the drug used for positive control mitomycin C (MMC) was commercially available from Kyowa Hakko Kogyo Co., Ltd., Japan.

Human gastric adenocarcinoma SGC-7901 xenograft was established and maintained. For the experiment, the xenograft fragments of diameter of about 2 mm were inoculated subcutaneously into the right submaxillary regions of nude mice. The animals were randomly divided into five groups five days after inoculation. NS and MMC (20 mg/kg) were given once a day i.p. in normal and positive control groups, respectively, while concentrated Q-can oral liquid was given in test groups once a day p.o., starting on the same day, at daily doses of 18, 36 and 72 mg branched-chain fatty acids per kg weight, respectively, for 14 days. Experiment was terminated 20 days post-implantation, and mice were sacrificed by spinal elongation. Tumors were removed and the weights of treated versus control tumors were compared. Inhibition rate was calculated. The experiment was repeated once.

Results

The results below indicated that Q-can oral liquid at effective doses of 18, 36 and 72 mg/kg given p.o. once a day for 14 days after tumor inoculation offered antitumor activity against human gastric adenocarcinoma SGC-7901 xenograft with no marked toxicity. The tumor inhibition rate increased with dosage of oral administration. The obvious shrinkage of the tumors was observed.

The results from the two tests (Test I and Test II are as follows):

Table 8. Effects of Q-can Oral Liquid on Human Gastric Adenocarcinoma Xenograft SGC-7901 Implanted Into Subcutaneous Areas of Nude Mice

| | | | | Test I | | | | |
|---|---|---|---|---|---|---|---|---|
| Group | dosage | route | schedule | Mice In./Fi. | Body wt. In./Fi. | Tumor wt. X ± SD, g | Inhibition % | p |
| NS | — | i.p. | Qd × 14 | 12/12 | 21.9/23.3 | 1.17 ± 0.45 | — | |
| MMC | 2.0 mg/kg | i.p. | Qd × 14 | 6/6 | 22.4/22.0 | 0.33 ± 0.24 | 71.49 | <0.01 |
| Q-can | 18 mg/kg | p.o. | Qd × 14 | 6/6 | 22.0/22.5 | 0.8 ± 0.42 | 31.19 | >0.05 |
| Q-can | 36 mg/kg | p.o. | Qd × 14 | 6/6 | 21.9/22.0 | 0.60 ± 0.45 | 48.23 | <0.05 |
| Q-can | 72 mg/kg | p.o. | Qd × 14 | 6/6 | 21.6/21.7 | 0.57 ± 0.35 | 51.28 | <0.05 |

| | | | | Test II | | | | |
|---|---|---|---|---|---|---|---|---|
| Group | dosage | route | schedule | Mice In./Fi. | Body wt. In./Fi. | Tumor wt. X ± SD, g | Inhibition % | p |
| NS | — | i.p. | Qd × 14 | 12/12 | 21.6/23.5 | 1.15 ± 0.30 | — | |
| MMC | 2.0 mg/kg | i.p. | Qd × 14 | 6/6 | 21.1/21.1 | 0.30 ± 0.33 | 73.51 | <0.01 |
| Q-can | 18 mg/kg | p.o. | Qd × 14 | 6/6 | 21.9/22.3 | 0.90 ± 0.59 | 21.58 | >0.05 |
| Q-can | 36 mg/kg | p.o. | Qd × 14 | 6/6 | 22.0/21.6 | 0.66 ± 0.49 | 42.47 | <0.05 |
| Q-can | 72 mg/kg | p.o. | Qd × 14 | 6/6 | 22.3/20.3 | 0.5 ± 0.37 | 55.45 | <0.01 |

B. Clinical Trials

EXAMPLE 13

Clinical Trial on Effects of (Q-can Oral Liquid on Supplementary Treatment of Cancer Methods The clinical trial of the effects of Q-can oral liquid as a supplementary treatment of cancer was carried out by the cooperation of five hospitals in China. 333 cases of cancer patients were involved and were randomly divided into two groups, chemotherapy and radiotherapy. The chemotherapy group included a control subgroup, which only took chemotherapy and contained 131 cases, and a test subgroup, which combined chemotherapy with Q-can oral liquid and contained 136 cases. The types of cancer involved included gastric, hepatic, esophageal, colon, pulmonary and mammary cancers, which were distributed similarly and comparably in the two subgroups (p>0.1). The radiotherapy group included a control subgroup (radiotherapy only, 32 cases) and a test subgroup (combination of radiotherapy and Q-can oral liquid, 34 cases). The types of cancers involved included nasopharyngeal and laryngeal cancers, which were distributed similarly and comparably in the two subgroups (p>0.1). Meanwhile, sex and age distribution of cancer patients in test and control subgroups was comparable (p>0.1).

The dosage of Q-can oral liquid for the two test subgroups was 80 ml×2 per day and it was given for two months.

The clinical observations and records were performed daily and filled in the unified observation forms. The changes of the deficiency syndrome, symptoms, blood routine plus platelet counts, the toxic reaction of chemotherapy or radiotherapy, and the side effects of Q-can oral liquid were recorded weekly. The cardiac, hepatic and renal functions, the living quality and the tumor size were examined or analyzed monthly. The serum, albumin and globulin, cellular immune functions (lymphocyte transformation, NK cell and subgroup composition of T-lymphocytes) and the humoral immunity were determined before and after the clinical trials.

Results

A. Effects on Clinical Symptoms

Four classes of therapeutic effects on deficiency syndrome were defined as:

Significant effect—the symptoms of the deficiency syndrome disappeared or got a significant favorable turn at the end of therapy;

Improvement—the symptoms got a favorable turn at the end of therapy;

Stability—the symptoms remained unchanged;

No effect—the symptoms became worse at the end of therapy.

In the chemotherapy group, the effectiveness rate of the test subgroup was 67.46% (significant effect plus improvement), which was significantly higher than that of the control subgroup (40.60%), $p<0.01$. In the radiotherapy group, the effectiveness rate of the test subgroup was significantly higher than that of the control subgroup, $p<0.05$ based on Ridit analysis.

TABLE 9

Symptom changes in the chemotherapy group

| sympton | sub-group | case | mitigation case (%) | stability case (%) | aggravation | p |
|---|---|---|---|---|---|---|
| appetite | Test | 72 | 49(68.06) | 18(25.00) | 5(6.94) | <0.01 |
|  | control | 81 | 18(22.22) | 33(40.74) | 30(37.04) |  |
| weakness | Test | 90 | 56(62.22) | 28(31.11) | 6(16.67) | <0.01 |
|  | control | 70 | 13(13.57) | 29(41.43) | 28(40.00) |  |

TABLE 10

Weight change in the chemotherapy group

| subgroup | case | increase case (%) | stability case (%) | decrease case (%) | p |
|---|---|---|---|---|---|
| test | 136 | 63(46.32) | 33(24.27) | 40(29.41) | <0.01 |
| control | 131 | 20(15.27) | 35(26.72) | 76(58.01) |  |

* increase and decrease were defined as more than 0.5 kg changes of body weight, and intermediate was stability.

B. Effect on Immune System

TABLE 11

Cellular immunity changes in the chemotherapy group

| item | subgroup | case | Pre-treat (X ± SD)% | Post-treat (X ± SD)% | p |
|---|---|---|---|---|---|
| LTT* | test | 65 | 55.95 ± 8.02 | 56.28 ± 8.55 | <0.01 |
|  | control | 75 | 55.85 ± 8.87 | 49.41 ± 12.21 |  |
| $CD_3$ | test | 30 | 43.53 ± 4.55 | 43.47 ± 5.10 | <0.01 |
|  | control | 30 | 45.47 ± 3.56 | 38.57 ± 4.50 |  |
| $CD_4$ | test | 30 | 44.07 ± 4.60 | 43.10 ± 5.13 | <0.01 |
|  | control | 30 | 42.60 ± 5.20 | 38.27 ± 5.62 |  |
| NK cell | test | 15 | 9.60 ± 5.11 | 12.00 ± 4.23 | <0.01 |
|  | control | 14 | 12.96 ± 4.31 | 10.80 ± 4.00 |  |

*LTT: Lymphocyte Transformation Test

TABLE 12

Humoral immunity changes in the chemotherapy/radiotherapy groups

| Item (g/L) | group | subgroup | case | Pre-treat (X ± SD) % | Post-treat (X ± SD) % | p |
|---|---|---|---|---|---|---|
| IgG | chemotherapy | test | 71 | 10.90 ± 4.69 | 11.92 ± 5.06 | <0.01 |
|  |  | control | 75 | 11.90 ± 4.38 | 11.05 ± 4.99 |  |
| IgA | chemotherapy | test | 72 | 1.63 ± 0.67 | 1.73 ± 1.32 | <0.01 |
|  |  | control | 75 | 1.65 ± 0.76 | 1.38 ± 0.76 |  |

TABLE 12-continued

Humoral immunity changes in the chemotherapy/radiotherapy groups

| Item (g/L) | group | subgroup | case | Pre-treat (X ± SD) % | Post-treat (X ± SD) % | p |
|---|---|---|---|---|---|---|
| | radiotherapy | test | 34 | 1.74 ± 1.31 | 2.39 ± 2.18 | <0.01 |
| | | control | 31 | 2.07 ± 1.03 | 1.88 ± 0.80 | |
| IgM | chemotherapy | test | 71 | 1.24 ± 0.59 | 1.55 ± 1.05 | <0.01 |
| | | control | 75 | 1.53 ± 0.78 | 1.30 ± 0.73 | |

The cellular and humoral immunity was enhanced in the test subgroup of combining chemotherapy and Q-can oral liquid. The concentration of IgA increased in the test subgroup of combining radiotherapy and Q-can oral liquid.

C. Effects on Chemotherapeutic Toxic Reaction

TABLE 13

Effects on toxic reaction of blood system

| item | subgroup | case | Pre-treat (X ± SD)% | Post-treat (X ± SD)% | p |
|---|---|---|---|---|---|
| WBC(×10$^9$) | test | 30 | 4.74 ± 1.21 | 5.45 ± 0.86 | <0.01 |
| | control | 30 | 5.29 ± 0.85 | 4.45 ± 0.80 | |
| Neutrophil cell | test | 30 | 3.20 ± 0.82 | 3.66 ± 0.69 | <0.01 |
| | control | 30 | 3.72 ± 0.58 | 3.09 ± 0.45 | |
| Hb(g/L) | test | 30 | 94.63 ± 18.00 | 96.89 ± 16.08 | <0.01 |
| | control | 30 | 103.67 ± 13.24 | 99.20 ± 11.63 | |
| platelet (×10$^9$/L) | test | 30 | 140.30 ± 4.88 | 160.03 ± 4.36 | <0.01 |
| | control | 30 | 157.33 ± 3.52 | 145.53 ± 5.33 | |

The blood routine and platelet quantity in the test subgroup dropped less than those in the control subgroup. This indicated that Q-can oral liquid can prevent the hemogram decrease caused by chemotherapy. Meanwhile, Q-can oral liquid was effective on the patients whose WBC and Hb were lower than normal before chemotherapy.

TABLE 14

Effects on hepatic function of the chemotherapy group

| | | SGPT (nmol/L, X + SD) | | |
|---|---|---|---|---|
| subgroup | case | pre-treat | post-treat | p |
| test | 89 | 460.06 ± 25.34 | 330.11 ± 245.01 | <0.05 |
| control | 84 | 261.47 ± 191.23 | 284.00 ± 217.30 | |

TABLE 15

Effects on serum protein of chemotherapy

| item | subgroup | case | pre-treat (g/L, X ± SD) | post-treat (g/L, X ± SD) | p |
|---|---|---|---|---|---|
| total protein | test | 101 | 65.31 ± 10.01 | 67.47 ± 5.99 | <0.01 |
| | control | 103 | 65.64 ± 6.53 | 64.20 ± 6.07 | |
| albumin | test | 107 | 38.78 ± 5.65 | 39.13 ± 5.26 | <0.01 |
| | control | 102 | 39.44 ± 4.74 | 38.18 ± 5.24 | |

SGPT decreased and serum total protein increased in the test subgroup of combining chemotherapy and Q-can oral liquid. The results showed that Q-can oral liquid could alleviate the damage of hepatic functions caused by chemotherapy and promote protein synthesis, thus protecting the liver.

TABLE 16

Effects on renal functions of the chemotherapy group

| sub-group | case | Blood urea nitrogen (nmol/L) Pre-treat | post-treat | case | Blood creatine (nmol/L) Pre-treat | Post-treat | p |
|---|---|---|---|---|---|---|---|
| test | 111 | 5.13 ± 2.95 | 4.95 ± 1.33 | 110 | 97.15 ± 30.64 | 97.99 ± 23.46 | <0.01 |
| control | 100 | 4.26 ± 1.03 | 5.04 ± 1.42 | 90 | 89.28 ± 22.13 | 107.08 ± 41.27 | |

Blood urea nitrogen and creatine decreased in the test group, which indicated that Q-can oral liquid could alleviate the damage of renal function caused by chemotherapy.

In summary, compared with the chemotherapy only treatment of 131 cases of cancer patients, the results of combinational treatment with Q-can oral liquid showed markedly enhanced therapeutical effects with statistical significance. These effects included amelioration of the deficiency syndrome, improvement of the appetite, weakness, living quality and immune functions, mitigation of the degree of leucopenic action induced by chemotherapy, alleviation of the low leukocyte count and the hemoglobin concentration which decreased after treatment, and protection of the hepatic and the renal functions. In comparison with the radiotherapy only treatment, the amelioration of the deficiency syndrome and increase of the serum IgG level were found in cancer patients, who were treated by combination of radiotherapy with Q-can oral liquid. Q-can oral liquid had no toxic effects on the blood, heart, liver and kidney. Thus, Q-can oral liquid can be used as a supplementary therapeutic agent for cancer patients.

EXAMPLE 14

Clinical Observation for 35 Cases of American Prostate Cancer Patients Treated by Q-can Oral Liquid The effect of Q-can oral liquid on PSA levels was tested for 8–18 weeks (average 14 weeks) in two hospitals in the USA, where an integrative approach to treating prostate cancer was applied. Patients were not on radiotherapy, chemotherapy, or hormonal treatment during the recording period and followed a customized nutritional protocol. At a daily dosage of 250 ml concentrated Q-can oral liquid (containing 300 mg specific branched-chain fatty acids), assay of PSA level was made for all patients. The average drop in PSA level was noted. It is also found that drops in PSA level of the patients who had higher pre-treat PSA level was more significant than those of the patients who had lower pre-treat PSA level.

TABLE 17

The effects of Q-can oral liquid on PSA level (mg/ml)

| Case Number | Pre-treat (mean ± SD) | Post-treat (mean ± SD) | p |
|---|---|---|---|
| 35 | 10.2 ± 10.72 | 7.45 ± 6.06 | <0.01 |

EXAMPLE 15

Industrial Process for Making Fermentation Liquid

This example describes one method of industrial production of Q-can oral liquid in a more detailed manner.

Medium composition is: soybean 40 kg (milling to milk and removing residue), $K_2HPO_4$ 200 mg, $CaCO_3$ 200 g, yeast extract 160 g, $MgSO_4$ 80 g, NaCl 80 g, $Na_2MoO_4$ 10 ppm. $ZnSO_4$ 10 ppm, $CoCl_2$ 5 ppm, $NaHNO_3$ 2 ppm, soybean oil (as antifoam addition) 4 kg, and add water to 400 kg totally.

The above media is put into a seeding tank and lead steam 120° C. for 30 minutes, then cooled to 30° C. Onto the seeding tank are inoculated 3 kg liquid cultures, which were cultured on the incubator shaker at 30° C. for 24 hours. Fermentation proceeds in the seeding tank for 24 hours, 30° C. temperature, 200 rpm agitation speed, and 1:1 (v/v min) aeration rate. After confirming no infection under microscope, it is then transferred into a 10 ton production fermenter for 48 hours, where compared to that in the seeding tank before, the media is ten times in quantity and the same percentage of the composition, and the same parameters of temperature, agitation speed and aeration rate are used. When fermentation is finished and no infection is confirmed under microscope, the temperature is increased to 100° C. to autoclave for 30 minutes. The cooled solution can be packaged and the packaged fermented solution is again autoclaved at 118° C. for 45 minutes. This is a semi-finished product waiting for quality inspection and final package as the Q-can oral liquid product.

Every description in the above specification of a numerical range and of a genus is intended to inherently include a description of all possible values and subranges within the range, and all possible species and subgenuses within the genus, respectively.

What is claimed is:

1. A method of treating cancer comprising administering to a cancer patient in need thereof an effective amount of at least one branched-chain unsaturated fatty acid, or a pharmaceutically acceptable salt thereof, or a pharmaceutically acceptable lipoprotein thereof, which is obtained by conjugation with a protein, wherein the branched-chain unsaturated fatty acid has the following formula:

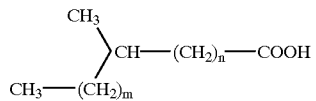

where n and m are independently integers, and n+m is between 0 and 46, inclusive, wherein n or m is at least 2, and at least one $CH_2-CH_2$ group in $(CH_2)_m$ or $(CH_2)_n$ is replaced with a $CH=CH$ group.

2. The method of claim 1, wherein the branched-chain fatty acid is obtained by isolation from fermentation or incubation products obtained from a bacteria strain containing said branched-chain fatty acid.

3. The method of claim 2, wherein the bacteria strain is from a genus selected from the group consisting of Stenotrophomonas, Xanthomonas, Flavobacterium, Capnocytophaga, Altermonas, Cytophage, Bacillus, Chryseobacterium, Empdobacter, Aurebacterium, Sphinggobacterium, Staphylococcus and Pseudomonas.

4. The method of claim 3, wherein the bacterial strain is Stenotrophomonas maltophilia.

5. The method of claim 4, wherein said bacterial strain is assigned ATCC 202105.

6. The method of claim 1, wherein the branched-chain fatty acid is obtained by chemical synthesis.

7. The method of claim 1, wherein the branched-chain fatty acid is obtained by extraction from natural materials.

8. The method of claim 1, wherein the branched-chain fatty acid is 15-metylhexadeceonic acid (iso 17:1 ω9c).

9. The method of claim 1, wherein the cancer treated is selected from the group consisting of leukemia, tongue cancer, colorectal cancer, breast cancer, prostate cancer, lung cancer, gastric cancer, hepatocarcinoma, melanocarcinoma, renal cancer, esophagus cancer and pancreas cancer.

10. The method of claim 1, wherein the branched chain fatty acid is administered as part of a fermentation product also containing a nutritive medium.

11. The method of claim 1, wherein the nutritive medium comprises a soybean medium.

12. The method of claim 11, wherein the soybean medium has the following formula:

| | |
|---|---|
| Soybean | 5–10% |
| or soybean miik or bean cake (by soybean wt.) | 5–15% |
| Yeast extract | 0.02–0.5% |
| or yeast powder | 0.02–0.5% |
| $CaCO_3$ | 0.05–0.25% |
| $K_2HPO_4$ | 0.02–0.10% |
| $MgSO_4$ | 0.01–0.05% |
| NaCl | 0.01–0.04% |
| $Na_2MoO_4$ | 5.0–30 ppm |
| $ZnSO_4$ | 2.5–15 ppm |
| $CoCl_2$ | 5.0–20 ppm. |

13. The method of claim 12, wherein the fermentation product is obtained from a culture of Stenotrophomonas maltophilia assigned ATCC 202105.

14. The method of claim 1, wherein the branched-chain fatty acid is administered in the form of an oral liquid, capsule, tablet, or injection.

15. A method of enhancing the treatment of cancer patients undergoing chemotherapy or radiotherapy comprising administering to a patient in need thereof an effective amount of at least one branched-chain unsaturated fatty acid, or a pharmaceutically acceptable salt thereof, or a pharmaceutically acceptable lipoprotein thereof, which is obtained by conjugation with a protein, wherein the branched-chain unsaturated fatty acid has the following formula:

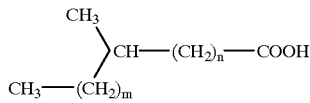

where n and m are independently integers, and n+m is between 0 and 46, inclusive, wherein n or m is at least 2, and at least one $CH_2$—$CH_2$ group in $(CH_2)_m$ or $(CH_2)_n$ is replaced with a CH=CH group.

16. A method of enhancing the treatment of cancer patients undergoing chemotherapy comprising administering to a patient in need thereof an effective amount of at least one branched-chain saturated or unsaturated fatty acid, or a pharmaceutically acceptable salt thereof, or a pharmaceutically acceptable lipoprotein thereof, which is obtained by conjugation with a protein, wherein the branched-chain fatty acid has the following formula:

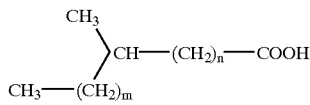

where n and m are independently integers, and n+m is between 0 and 46, inclusive, with the proviso that when said acid is unsaturated, m or n is at least 2, and at least one $CH_2$—$CH_2$ group in $(CH_2)_m$ or $(CH_2)_n$ is replaced with a CH=CH group, wherein at least one of the following symptoms is treated: alleviation of low leukocyte count and hemoglobin concentration which is decreased after treatment, and protection of hepatic and renal functions.

17. A method of enhancing the treatment of cancer patients undergoing radiotherapy comprising administering to a patient in need thereof an effective amount of at least one branched-chain saturated or unsaturated fatty acid, or a pharmaceutically acceptable salt thereof, or a pharmaceutically acceptable lipoprotein thereof, which is obtained by conjugation with a protein, wherein the branched-chain fatty acid has the following formula:

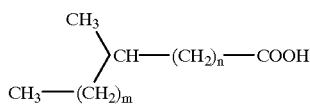

where n and m are independently integers, and n+m is between 0 and 46, inclusive, with the proviso that when said acid is unsaturated, m or n is at least 2, and at least one $CH_2$—$CH_2$ group in $(CH_2)_m$ or $(CH_2)_n$ is replaced with a CH=CH group, wherein at least one of the following symptoms is treated: amelioration of deficiency syndrome and increase of serum IgG level.

18. A method of treating prostate cancer comprising administering to a patient in need thereof a PSA-lowering effective amount of at least one branched-chain saturated or unsaturated fatty acid, or a pharmaceutically acceptable salt thereof, or a pharmaceutically acceptable lipoprotein thereof, which is obtained by conjugation with a protein, wherein the branched-chain fatty acid has the following formula:

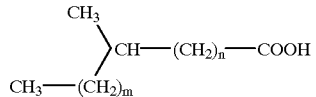

where n and m are independently integers, and n+m is between 0 and 46, inclusive, with the proviso that when said acid is unsaturated, m or n is at least 2, and at least one $CH_2$—$CH_2$ group in $(CH_2)_m$ or $(CH_2)_n$ is replaced with a CH=CH group, wherein the branched chain fatty acid is administered as part of a fermentation product also containing a nutritive medium.

19. The method of claim 1, wherein the effective amount is an amount effective to induce apoptosis of cancer cells.

20. A method of treating cancer comprising administering to a cancer patient in need thereof an effective amount of at least one branched-chain saturated or unsaturated fatty acid, or a pharmaceutically acceptable salt thereof, or a pharmaceutically acceptable lipoprotein thereof, which is obtained by conjugation with a protein, wherein the branched-chain fatty acid has the following formula:

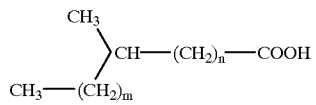

where n and m are independently integers, and n+m is between 0 and 46, inclusive, with the proviso that when said acid is unsaturated, n or m is at least 2, and at least one $CH_2$—$CH_2$ group in $(CH_2)_m$ or $(CH_2)_n$ is replaced with a CH=CH group, and wherein the branched chain fatty acid is administered as part of a fermentation product also containing a nutritive medium.

21. The method of claim 20, wherein the nutritive medium comprises a soybean medium.

22. The method of claim 21, wherein the soybean medium has the following formula:

| | |
|---|---|
| Soybean | 5-10% |
| or soybean milk or bean cake (by soybean wt.) | 5-15% |
| Yeast extract | 0.02-0.5% |
| or yeast powder | 0.02-0.5% |
| $CaCO_3$ | 0.05-0.25% |
| $K_2HPO_4$ | 0.02-0.10% |
| $MgSO_4$ | 0.01-0.05% |
| NaCl | 0.01-0.04% |
| $Na_2MoO_4$ | 5.0-30 ppm |
| $ZnSO_4$ | 2.5-15 ppm |
| $CoCl_2$ | 5.0-20 ppm. |

23. The method of claim 22, wherein the fermentation product is obtained from a culture of *Stenotrophomonas maltophilia* assigned ATCC 202105.

* * * * *